United States Patent [19]

Lundell et al.

[11] Patent Number: 5,796,325
[45] Date of Patent: Aug. 18, 1998

[54] CHARGING COIL CORE INSERT FOR ELECTRIC TOOTHBRUSHES

[75] Inventors: William G. Lundell; Gerald K. Brewer, both of Redmond, Wash.

[73] Assignee: Optiva Corporation, Bellevue, Wash.

[21] Appl. No.: 706,439

[22] Filed: Aug. 30, 1996

[51] Int. Cl.⁶ .................. H01F 27/02; H01F 27/24
[52] U.S. Cl. .................. 336/233; 336/83; 336/DIG. 2
[58] Field of Search .................. 336/DIG. 2, 232, 336/233, 83

[56] References Cited

U.S. PATENT DOCUMENTS

| | | | |
|---|---|---|---|
| 3,277,358 | 10/1966 | Nicholl | 336/90 |
| 3,418,552 | 12/1968 | Holmes | 336/DIG. 2 |
| 5,150,492 | 9/1992 | Suroff | 15/22.1 |
| 5,165,131 | 11/1992 | Staar | 15/22.1 |

Primary Examiner—Michael L. Gellner
Assistant Examiner—Anh Mai
Attorney, Agent, or Firm—Jensen & Puntigam, P.S.

[57] ABSTRACT

A coil insert for use with a secondary coil portion of a charging system for an electric toothbrush. The secondary coil is positioned within the handle of the toothbrush. The insert includes a first portion which is configured to fit in the central opening of the secondary coil and a base portion which extends out from the secondary coil. The insert has enough weight, approximately one ounce, to significantly dampen the vibrational effects caused by operation of the toothbrush. The steel peen is sufficiently small so as to not absorb any energy from the charging coil during operation of the charging system and to increase coupling efficiency between the primary and secondary charging coils.

6 Claims, 1 Drawing Sheet

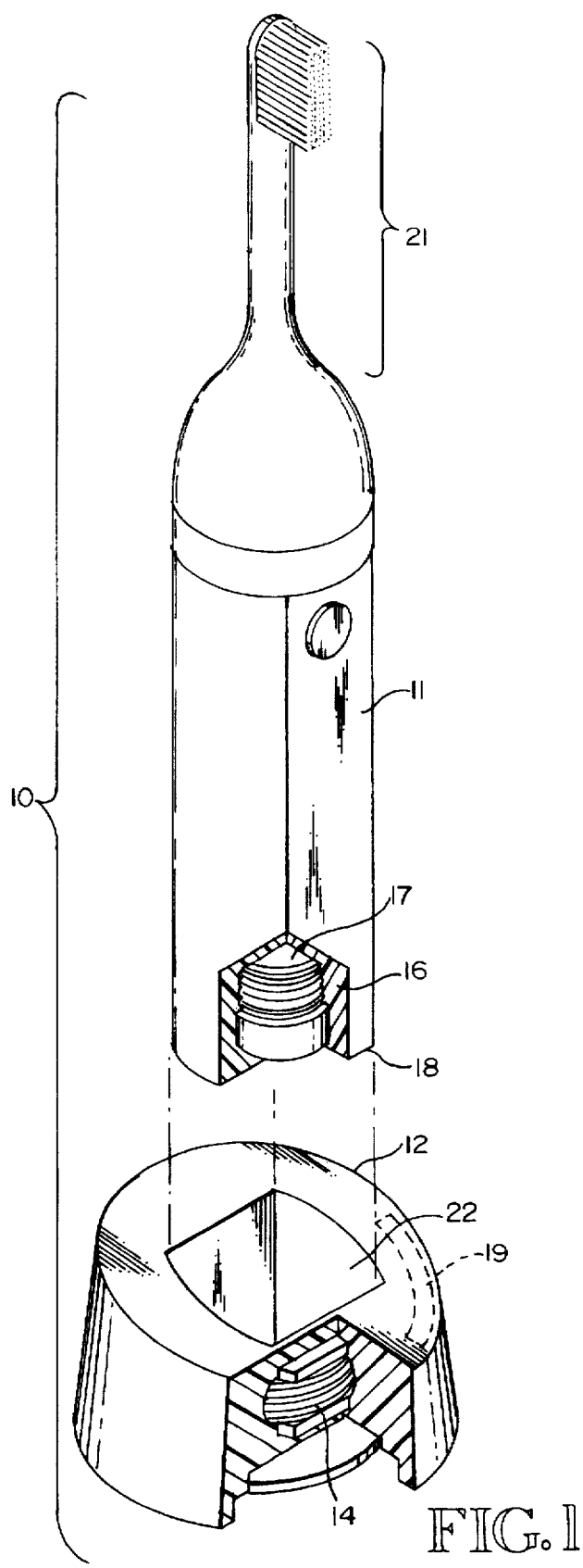
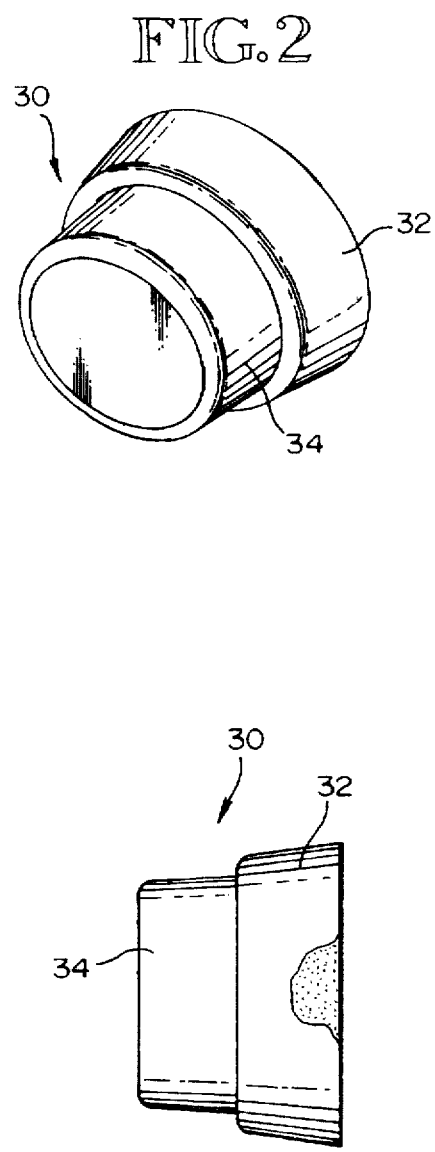
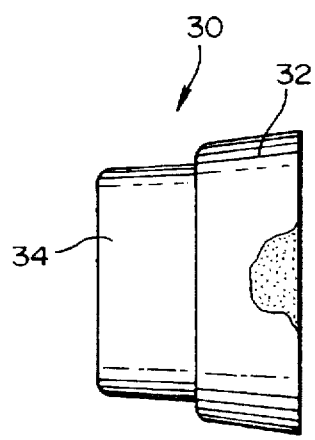

CHARGING COIL CORE INSERT FOR ELECTRIC TOOTHBRUSHES

TECHNICAL FIELD

This invention relates generally to charging systems for electric toothbrushes, and more specifically concerns a coil core insert used in such a charging system.

BACKGROUND OF THE INVENTION

Electric toothbrushes, i.e. those toothbrushes powered by electrical current, are generally well known, although they vary widely in their operating parameters, including frequency of vibration and the amplitude of movement of the brush element. Electric toothbrushes may be powered from a wall outlet, or they may be battery powered. An example of an electric toothbrush using a battery and an electromagnetic motor is shown in U.S. Pat. No. 5,189,751, which is owned by the assignee of the present invention and which is hereby incorporated by reference. Newer battery-powered toothbrushes, including the '751 toothbrush, have batteries which are rechargeable, and such toothbrushes are usually provided with a charging unit in which the toothbrush can be placed for extended times for charging.

The charging system will typically include a primary coil in the charging unit and a secondary coil within the toothbrush itself. The charging unit and the toothbrush are designed such that when the toothbrush is placed in the charging unit, there will be electrical coupling between the two coils, with the induced current in the secondary coil providing the charging current for the battery in the toothbrush. In certain such charging system implementations using line frequency, i.e. 50–60 Hz, however, the coupling efficiency is rather poor. It may take as much as 30 hours to fully charge the batteries, upon purchase of the toothbrush or if the batteries ever become completely discharged. Even normal charging following periods of use requires a substantial amount of time for the batteries to become fully charged. A fully charged battery is of course important for proper operation of an electric toothbrush.

Using a much higher frequency charging current will significantly increase the efficiency of the charging, and will result in a corresponding reduction in the respective sizes of the coils. However, such a change results in a significant reduction in weight at the lower end of the toothbrush, increasing the vibration of the unit. Attempting to increase the weight at the lower end of the toothbrush with either a solid slug or a ferrite core has been found to either adversely affect the coupling between the two coils or be too expensive.

DISCLOSURE OF THE INVENTION

Accordingly, the present invention is a coil core insert for use in a secondary charging coil in an electric toothbrush for a high frequency charging system therefor, comprising: a core insert for the secondary charging coil, comprising a mixture of (1) steel peen, the peen being small enough in size so as to absorb substantially no current from the charging coil and (2) a binder material for binding the peen together in a solid mass.

BRIEF DESCRIPTION OF THE DRAWINGS

FIG. 1 is a partially exploded, partially cutaway view showing an electric toothbrush and a charging system for the toothbrush, the charging system including the coil core insert of the present invention.

FIG. 2 is an isometric view of the coil core insert of FIG. 1.

FIG. 3 is a side elevational view of the coil core insert of FIGS. 1 and 2.

BEST MODE FOR CARRYING OUT THE INVENTION

FIG. 1 shows generally an electric toothbrush system, comprising a toothbrush 10, including a handle portion 11 and a brush/arm portion 21, and a charging unit or base 12 which can be plugged into a wall outlet for 60 Hz, 120 volt power, or alternatively, 50 Hz at 230 volts. The charging system for the toothbrush includes a primary coil 14 positioned in the base 12 and a secondary coil 16 which is positioned near the lower end 18 of the handle of the toothbrush 10. Charging unit 12 also includes a circuit 19 to convert the frequency of the line current from 50/60 Hz to a higher frequency, which in the embodiment shown and described is 90 kHz. It should be understood, however, that the specific high frequency disclosed can be varied, i.e. for instance within the range of 80–100 kHz, while still retaining the general advantages of high frequency coupling, discussed below.

The charging unit 12 and the primary coil 14 therein are configured and arranged so that there is defined in charging unit 12 an opening 22, central of primary coil 14. Opening 22 is large enough to accommodate the handle 11 of toothbrush 10 so that when the toothbrush is not being used, it may be conveniently positioned upright in the charging unit.

In the embodiment shown, secondary coil 16 in the toothbrush 10 is wound on a bobbin 17 which is slightly greater than one inch in diameter and approximately ⅜ inch high. The coil includes connections (not shown) to the rechargeable batteries in the handle of the toothbrush. In the embodiment shown, secondary coil 16 has approximately 52 turns of copper wire.

As indicated in the background portion of the application, however, the high frequency charging coil arrangement described above has some disadvantages, including a relatively low handle weight for the toothbrush, which results in a significant vibration when the toothbrush is in use. In those embodiments which use a charging frequency of 50–60 Hz, the additional size (and hence weight) of the coil necessitated by use of that charging frequency tended to dampen the vibration of the handle caused by movement of the brush element and supporting arm 21 at the other end of the toothbrush. Placing a solid slug of iron or other heavy material within the core of coil 16 in order to provide additional weight significantly reduces the efficiency of the coupling between the coils and is hence undesirable. The use of a ferrite core, while providing additional weight without significantly harming coupling efficiency, is quite expensive and therefore an impractical solution.

In the embodiment of the present invention shown, a special core insert is made from steel peen (shot). Such steel shot, which is primarily useful for surface treatment of metals, is readily commercially available and quite inexpensive. A coil insert shown generally at 30 is manufactured from a combination of such peen and a binder material which is used to bind or join the steel shot into a solid unit.

In the embodiment shown, the steel shot is within a range of 0.02–0.08 inches in diameter, preferably approximately 0.04 inches in diameter. This size can be varied somewhat, although it must be small enough not to rob any current induced into the secondary coil from the primary coil of the charging system. This is important in maintaining the efficiency of the coupling, which is the primary reason for use of high frequency current. In the embodiment shown, the binder material is a conventional epoxy which is mixed with a surfactant so that it wicks readily with the steel shot when poured over the peen in a mold, covering all of the peen and leaving no uncovered surfaces or interior holes. Basically, it provides an encapsulating structure for the shot, capturing it into a molded unit. If a surfactant is not used, then the epoxy or other binder material and the shot must be mixed to thoroughly provide the same, complete coverage/encapsulation. The mixture of the epoxy and the steel shot in the molds is then cured. The coil core inserts may then readily be removed from the mold and used.

In the embodiment shown, referring to FIGS. 2 and 3, the coil core insert, shown generally at 30, includes a lower base portion 32 and an upper, core portion 34. The sides of both the base portion and the core portion, as well as the upper peripheral edges thereof, are slightly relieved, as shown in FIG. 3 in particular, in order to facilitate removal of the insert 30 from the mold. However, such a relieved configuration is not necessary to the function of the insert. The core portion 34 in the embodiment shown has a height of approximately 0.65 inches and a diameter of approximately 0.805 inches. This configuration and size matches with the internal diameter of coil bobbin 17, both with respect to diameter and height. There should be a fairly snug fit between core portion 34 and the internal opening of bobbin 17.

The core portion 34 alone, however, does not provide the most advantageous amount of additional weight desired. The total weight of insert 30 in the embodiment shown is approximately one ounce. Base portion 32, which is outside bobbin 24, such as can be seen from FIG. 1, provides the additional weight desired. Base portion 32 in the embodiment shown has a height of approximately 0.65 inches and a diameter of approximately 1.06 inches. The size and configuration of base portion 32 may of course be varied, depending upon the amount of additional weight desired. However, for the embodiment shown, the configuration and size of the insert provides the desired total weight of approximately one ounce, which is sufficient to reduce or significantly lessen the disadvantageous vibrational effect caused by the movement of the brush element and arm 21 at the other end of the toothbrush.

The advantages of using steel shot include cost (it is quite inexpensive) and enhancement of coupling between the primary and secondary coils. In the particular embodiment shown, an improvement in coupling efficiency of 20-35% has been achieved. A ferrite core, while not adversely affecting coupling, will not significantly improve coupling in the structure shown and is substantially more expensive.

Hence, the use of the coil insert 30 shown and described above provides the additional weight necessary to lessen the vibrational effect caused by action of the toothbrush, while also providing improved coupling between the primary and secondary coils, so that maximum advantage can be obtained from a high frequency charging system, which as mentioned above, results in significantly improved charging times and energy transfer efficiency relative to a lower charging frequency, i.e. 60 Hz.

Although a preferred embodiment of the invention has been disclosed herein for illustration, it should be understood that various changes, modifications and substitutions may be incorporated in such embodiment without departing from the spirit of the invention, which is defined by the claims which follow:

What is claimed is:

1. A coil core insert for use in a secondary charging coil in an electric toothbrush for a high frequency charging system therefor, comprising:

a core insert for the secondary charging coil, comprising a solid mixture of 1) steel shot, the shot being small enough in size so as to absorb substantially no current from the charging coil and 2) a binder material for binding the shot together in a solid mass.

2. An article of claim 1, wherein the shot is of such a size that an increase in coupling efficiency occurs between the primary charging coil and the secondary charging coil relative to the coupling efficiency in the absence of a core insert for the secondary charging coil.

3. An article of claim 2, wherein the increase in coupling efficiency is at least 20%.

4. An article of claim 1, wherein the insert comprises first and second portions, the first portion being configured and arranged to fit snugly within a central opening of the secondary charging coil, the second portion being outside of the coil when the first portion of the insert is positioned within the central opening of the coil, the second portion providing additional weight for the insert.

5. An article of claim 4 wherein the core insert is sufficiently heavy to dampen vibration in a lower end of the toothbrush when the toothbrush is in operation.

6. An article of claim 1, wherein the steel shot are in the range of 0.02 to 0.08 inches in diameter.

* * * * *